US00PP27569P3

(12) United States Plant Patent
Egger

(10) Patent No.: US PP27,569 P3
(45) Date of Patent: Jan. 17, 2017

(54) **×*HEUCHERELLA* PLANT NAMED 'AUTUMN CASCADE'**

(50) Latin Name: ×***Heucherella* hybrid**
Varietal Denomination: Autumn Cascade

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 88 days.

(21) Appl. No.: 14/545,244

(22) Filed: Apr. 13, 2015

(65) Prior Publication Data

US 2016/0302347 P1 Oct. 13, 2016

(51) Int. Cl.
*A01H 5/12* (2006.01)

(52) U.S. Cl.
USPC ..... Plt./441

(58) Field of Classification Search
USPC ..... Plt./441
See application file for complete search history.

(56) References Cited

PUBLICATIONS

New Plants and Flowers Two Recent Sneak Peak introductions Jan. 15, 2015, retrieved on Aug. 18, 2016, retrieved from the Internet at <http://www.newplantsandflowers.com/two-recent-sneak-peek-introductions/> 2 pp.*

* cited by examiner

*Primary Examiner* — June Hwu
(74) *Attorney, Agent, or Firm* — Klarquist Sparkman, LLP; Sheree Rybak

(57) ABSTRACT

A new and distinct ×*Heucherella* plant substantially as shown and described, characterized by red to yellow green to rust colored leaves with a dark pattern along veins and a white veil, deeply lobed leaves with wide sinus, a low, dense, vigorously trailing habit with good branching, and excellent vigor.

2 Drawing Sheets

Botanical denomination: ×*Heucherella* hybrid.

Variety designation: 'Autumn Cascade'.

Cross reference to siblings: ×*Heucherella* 'Gold Cascade' (U.S. Plant Pat. No. 25,738), ×*Heucherella* 'Copper Cascade' (U.S. Plant Pat. No. 25,722).

BACKGROUND OF THE INVENTION

The present invention relates to a new and distinct cultivar of ×*Heucherella* and given the cultivar name of 'Autumn Cascade'. ×*Heucherella* is in the family Saxifragaceae. ×*Heucherella* 'Autumn Cascade' originated from a controlled cross between *Heuchera* 'K521-1-1' (a proprietary, unpatented, unreleased *Heuchera*), as the seed parent, and *Tiarella* '42-2' (a proprietary, unpatented, unreleased *Tiarella*), as the pollen parent.

Compared to the seed parent *Heuchera* 'K521-1-1', the new cultivar is trailing with rust colored, deeply lobed leaves with red to brown centers rather than clumping with pink to khaki colored, shallowly lobed leaves.

Compared to the pollen parent *Tiarella* '42-2', the new cultivar has rust colored leaves rather than green.

Compared to its sibling, ×*Heucherella* 'Gold Cascade', the new cultivar has rust colored foliage that is deeply lobed rather than chartreuse and shallowly lobed.

Compared to its sibling, ×*Heucherella* 'Copper Cascade', the new cultivar has rust colored foliage that is deeply lobed rather than red to rust and shallowly lobed.

Compared to ×*Heucherella* 'Redstone Falls', U.S. Plant Pat. No. 22,394, the new cultivar has a lower, denser habit and leaves with more prominent lobing due to wider sinus on between the lobes and deeper secondary lobes.

This new ×*Heucherella* is uniquely characterized by:

1. red to yellow green to rust colored leaves with a dark pattern along veins and a white veil,
2. deeply lobed leaves with wide sinus,
3. a low, dense, vigorously trailing habit with good branching, and
4. excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a seven-month-old ×*Heucherella* 'Autumn Cascade' in a one gallon container grown outside in shade in early July in Canby, Oreg.

FIG. 2 shows an eight-month-old plant in the trial field grown in part shade in late July in Canby, Oreg.

DETAILED PLANT DESCRIPTION

Figure 3:
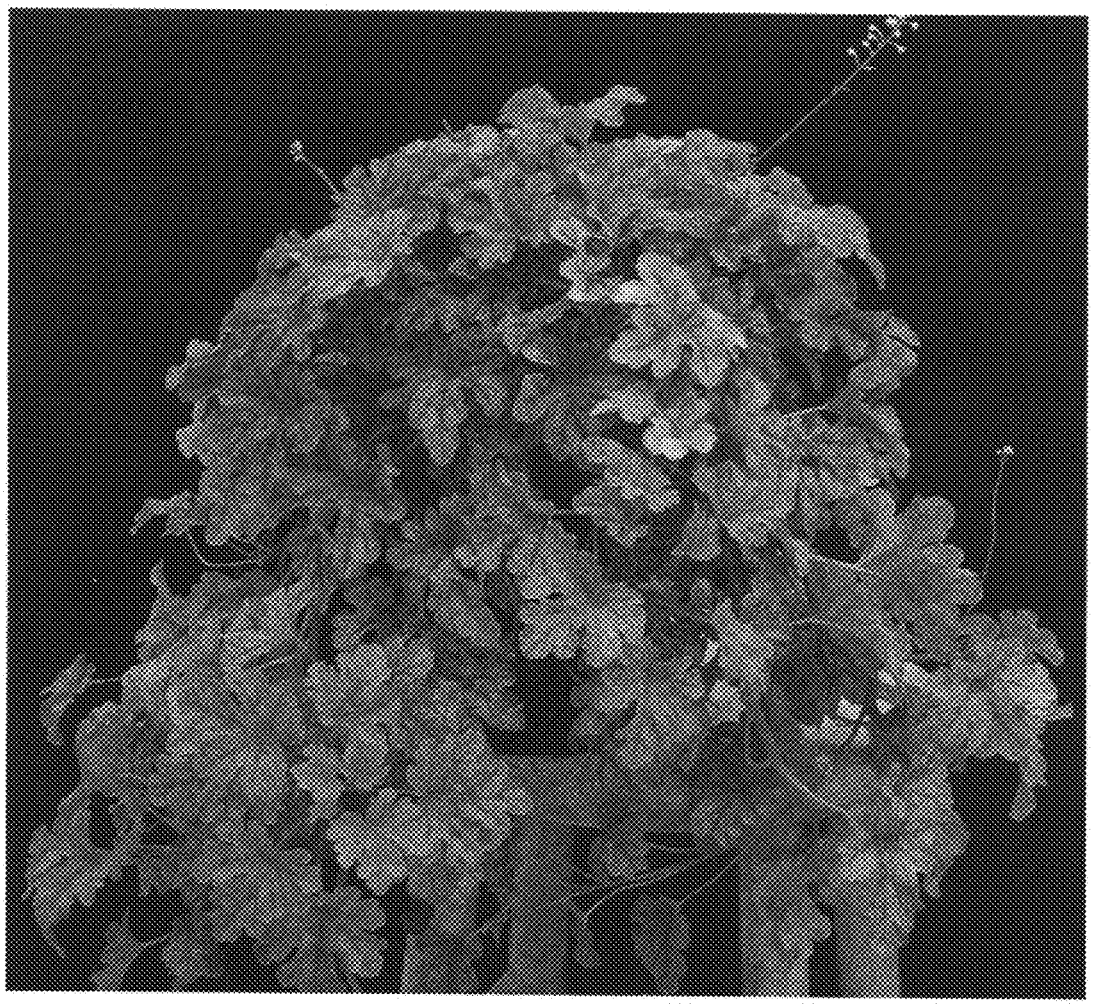
FIG. 3 shows a ten-month-old plant in a one gallon container grown outside in shade in mid-October in Canby, Oreg.

The following is a detailed description of the new ×*Heucherella* cultivar based on observations of 10-month-old specimens grown outside in a one gallon containers in shade October in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition, 2007.

Plant:

*Form*.—Basal rosette with trailing stems, herbaceous perennial.

*Hardiness*.—USDA Zone 4 to 9.

*Size*.—15 cm tall from top of the foliage to the ground and 40 cm wide before trailing down.

*Habit*.—Mounding with 12 crowns and trailing with 7 stems.

*Vigor*.—Excellent.

*Roots*.—Fibrous, freely branching, fine, and White 155A in color.

Stem:

*Size*.—4.5 mm wide and grows to 70 cm long.

*Internode length*.—1 cm to 4 cm.

*Surface texture*.—Glandular hairs.

*Stem color*.—Greyed Purple 187B.

Leaf:

*Type*.—Simple.

*Arrangement*.—Rosette and alternate.

*Shape*.—Broadly ovate.

*Lobing/division*.—7 palmate lobes with broad sinuses and shallower secondary lobes.

*Venation*.—Palmate.

*Margins*.—Broadly crenate and slightly undulate.

*Apex*.—Mucronulate.

*Base*.—Cordate, sometimes overlapping.

*Glossiness*.—Weak.

*Blade size*.—Basal and stem both grow to 10.5 cm long and 10 cm wide.

*Surface texture*.—Glandular hairs on both surfaces.

*Petiole description*.—On basal leaf grows to 16 cm long and 2.5 mm wide, on stem grows to 11 cm long and 3 mm wide, both with glandular hairs and Greyed Orange 177A.

*Leaf color*.—Variable depending on age, light, and temperature; spring topside Greyed Red 178B with a thin white veil NN155B and dark splatter pattern near veins Greyed Purple 187A, bottom side between Red Purple 59A and bottom side Greyed Purple 187B; summer young leaves topside Greyed Red 178B with a thin white veil NN155B and dark splatter pattern near veins Greyed Purple 187A with bottom side Greyed Purple 187B, summer older leaves topside between Greyed Orange 166D and Greyed Yellow 161A with a thin white veil NN155B and the dark splatter pattern Greyed Purple 187B, bottom side Greyed Purple 183D; fall young leaves topside Greyed Red 178B to 177A with a thin white veil NN155B and dark splatter pattern near veins Greyed Purple 187A maturing to Yellow Green 146A with pattern 187A, bottom side 187B; winter leaves topside Greyed Red 182B with leaf edge 183A and pattern prominent 187A, bottom side 182A.

Inflorescence:

*Size*.—Usually 13.5 cm long and 4 mm wide.

*Type*.—Upright to semi-upright raceme.

*Number of flowers per raceme*.—About 85.

*Density of flowers in raceme*.—Medium.

*Number of racemes*.—About 25.

*Peduncle*.—Grows to 30 cm long, 2.5 mm wide at base, 1 to 2 petiolate floral leaves (blades grow to 3.2 cm long and 4 cm wide, ovate, 3 to 5 lobed, tip mucronulate, margin crenate, base truncate to attenuate, glandular hairs on both sides, Greyed Red 178A with a thin white veil NN155B, sometimes splatter patterned 187A), glandular hairs, Greyed Purple 187B.

*Pedicel*.—Grows to 4 mm long, with glandular hairs, Greyed Purple 183A.

*Bloom period*.—July to October in Canby, Oreg.

Flower bud:

*Size*.—2.5 mm long and 2 mm wide.

*Description*.—Glandular puberulent, ovoid, side-facing.

*Color*.—White 155A.

Flower:

*Type*.—Imperfect.

*Shape*.—Campanulate.

*Attitude*.—Usually side-facing.

*Size*.—4 mm deep and 7 mm wide.

*Petal description*.—5 in number, stellate, linear to spatulate, 3 mm long and 0.5 mm wide, reflexed slightly, tip acuminate, base attenuate, margin entire, glabrous and White NN155B on both sides.

*Calyx description*.—3 mm deep and 4 mm wide, campanulate, with 5 lobes, divided ½ way to the base, lobes 2 mm long and 1.5 mm wide, oblong, glandular hairs on back sides, glabrous inside, tip obtuse, margin entire, White NN155B on both sides.

*Stamen description*.—10, 3 mm long, filament 3 mm long and White NN155B, anthers Greyed Orange 177A, no pollen.

*Pistil description*.—1 in number, grows to 4.5 mm long and 1.5 mm wide, ovaries grow to 1.5 mm long and 1.5 wide, White NN155B, beaked style 3 mm long White NN155B.

*Fragrance*.—None.

*Lastingness*.—Each raceme blooms for about 2 weeks on the plant.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

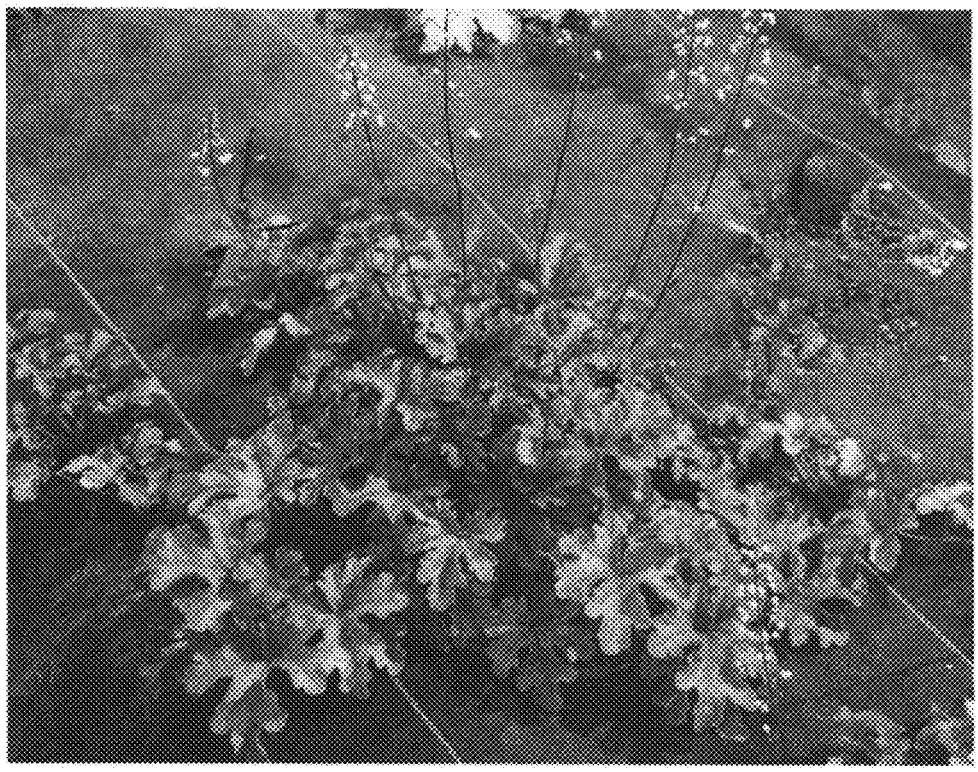

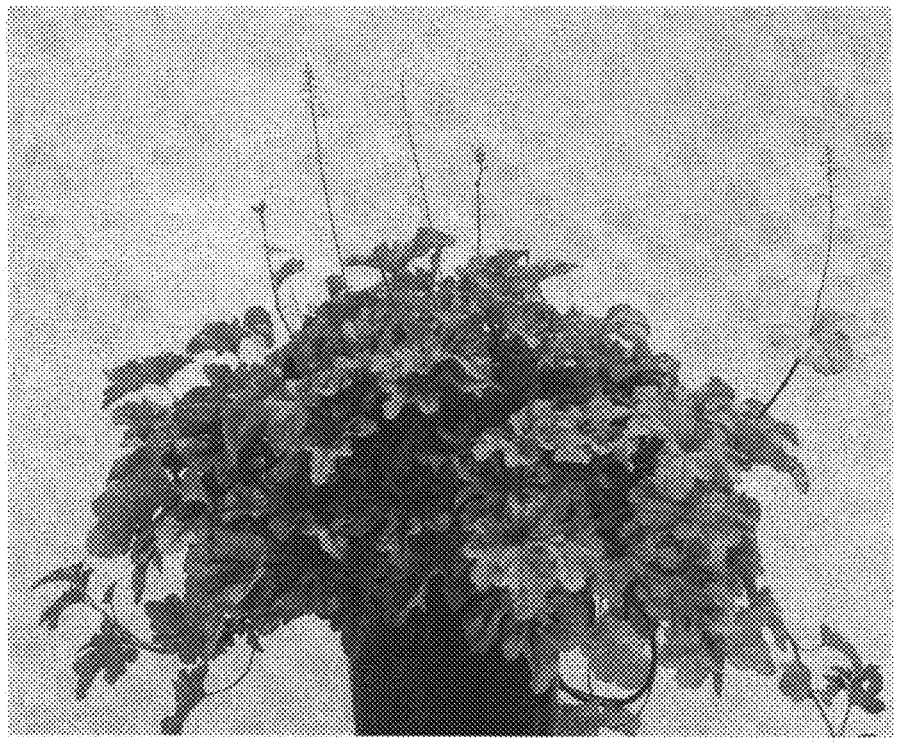
FIG. 1 above, FIG. 2 below